US00PP32564P2

(12) United States Plant Patent
Smit

(10) Patent No.: US PP32,564 P2
(45) Date of Patent: Dec. 1, 2020

(54) ***PEPEROMIA* PLANT NAMED 'EC-PEPE-1904'**

(50) Latin Name: *Peperomia caperata*
Varietal Denomination: EC-PEPE-1904

(71) Applicant: Eden Collection, BV, Sappemeer (NL)

(72) Inventor: Obed Smit, Sappemeer (NL)

(73) Assignee: Eden Collection B.V. (NL)

( * ) Notice: Subject to any disclaimer, the term of this patent is extended or adjusted under 35 U.S.C. 154(b) by 0 days.

(21) Appl. No.: 16/873,173

(22) Filed: Feb. 18, 2020

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
CPC ..... A01H 5/12; A01H 6/00
See application file for complete search history.

*Primary Examiner* — Keith O. Robinson
(74) *Attorney, Agent, or Firm* — Cassandra Bright

(57) ABSTRACT

A new and distinct cultivar of *Peperomia* plant named 'EC-PEPE-1904' is disclosed, characterized by a combination of a rosette-shaped plant habit, and round foliage colored shades of greyed-green with dark greyed-green venation. The new variety is a *Peperomia*, typically used as an ornamental plant.

2 Drawing Sheets

Figure 1:
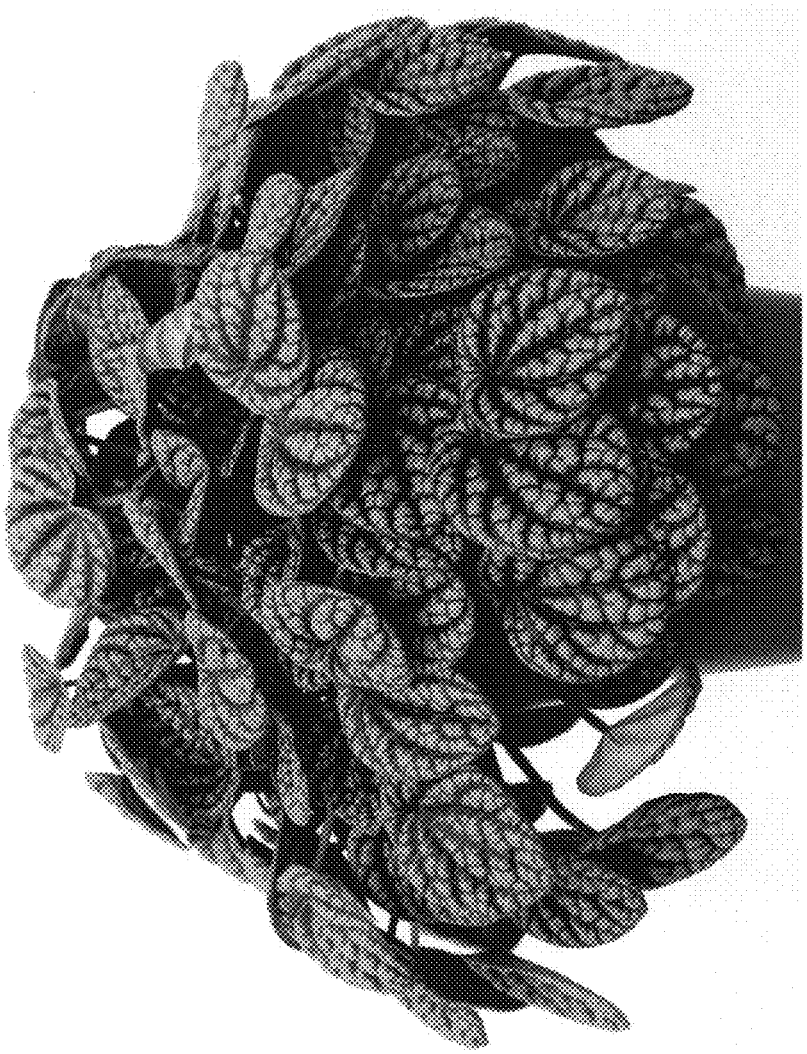

Latin name of the genus and species: *Peperomia caperata.*

Variety denomination: 'EC-PEPE-1904'.

BACKGROUND OF THE INVENTION

The new cultivar is a product of a planned breeding program. The new variety was selected as a seedling resulting from the crossing of two unnamed, unpatented varieties of *Peperomia caperata*. The crossing was made by the inventor, Obed J. Smit in 2014. 'EC-PEPE-1904' was selected by the inventor in 2017 at a commercial greenhouse in Sappemeer, the Netherlands.

Asexual reproduction of the new cultivar 'EC-PEPE-1904' by leaf cuttings was first performed in Sappemeer, the Netherlands at a commercial greenhouse in March 2017 and has shown that the unique features of this cultivar are stable and reproduced true to type through successive generations.

SUMMARY OF THE INVENTION

The cultivar 'EC-PEPE-1904' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-1904'. These characteristics in combination distinguish 'EC-PEPE-1904' as a new and distinct *Peperomia* cultivar:

1. Round-shaped leaves.
2. Grey-green foliage with dark greyed-green veins.
3. Rosette-shaped plant habit.

PARENT COMPARISON

Plants of the new cultivar 'EC-PEPE-1904' are similar to plants of the female parent in most horticultural characteristics, however, plants of the new cultivar 'EC-PEPE-1904' differ in the following characteristics:

1. The new variety has round leaves, while the seed parent has less rounded leaves with a pointed tip.
2. Leaf upper side of the new variety has different shades of grey-green, while leaves of the seed parent are more solid grey.
3. The new variety has puckered leaves with deeper-lying veins, while the seed parent has smooth leaves.
4. The new variety has irregular veins, while the seed parent has parallel veins.

Plants of the new cultivar 'EC-PEPE-1904' are similar to plants of the male parent in most horticultural characteristics, however, plants of the new cultivar 'EC-PEPE-1904' differ in the following characteristics:

1. Leaf upper side of the new variety has different shades of grey-green, while leaf upper side of the pollen parent is green.
2. Leaves of the new variety are larger than leaves of the pollen parent.
3. The new variety has a more dense rosette habit than the pollen parent.

COMMERCIAL COMPARISON

Plants of the new cultivar 'EC-PEPE-1904' are similar to plants of the commercial variety *Peperomia caperata* 'Eden Rosso', U.S. Plant Pat. No. 24,379. However, plants of the new cultivar differ in the following characteristics:

1. Leaf upper side of the new variety has different shades of grey-green, while the leaf upper side of this comparator is dark green.
2. Leaf under side of the new variety is green, while leaf under side of this comparator is red.
3. Leaves of the new variety are round, while leaves of this comparator are oblong with pointed tip.

Plants of the new cultivar 'EC-PEPE-1904' are similar to plants of the variety *Peperomia* 'Napoli Nights', U.S. Plant Pat. No. 29,416. However, plants of the new cultivar differ in the following characteristics:

1. Leaf upper side of the new variety has different shades of grey-green, while the leaf upper side of this comparator is evenly grey.
2. Leaves of the new variety are round, while leaves of this comparator are oblong with a pointed tip.

BRIEF DESCRIPTION OF THE PHOTOGRAPHS

The accompanying photograph in FIG. 1 illustrates in full color a typical blooming plant of 'EC-PEPE-1904' grown in a greenhouse. The plant is approximately 30 weeks of age.

Figure 2:
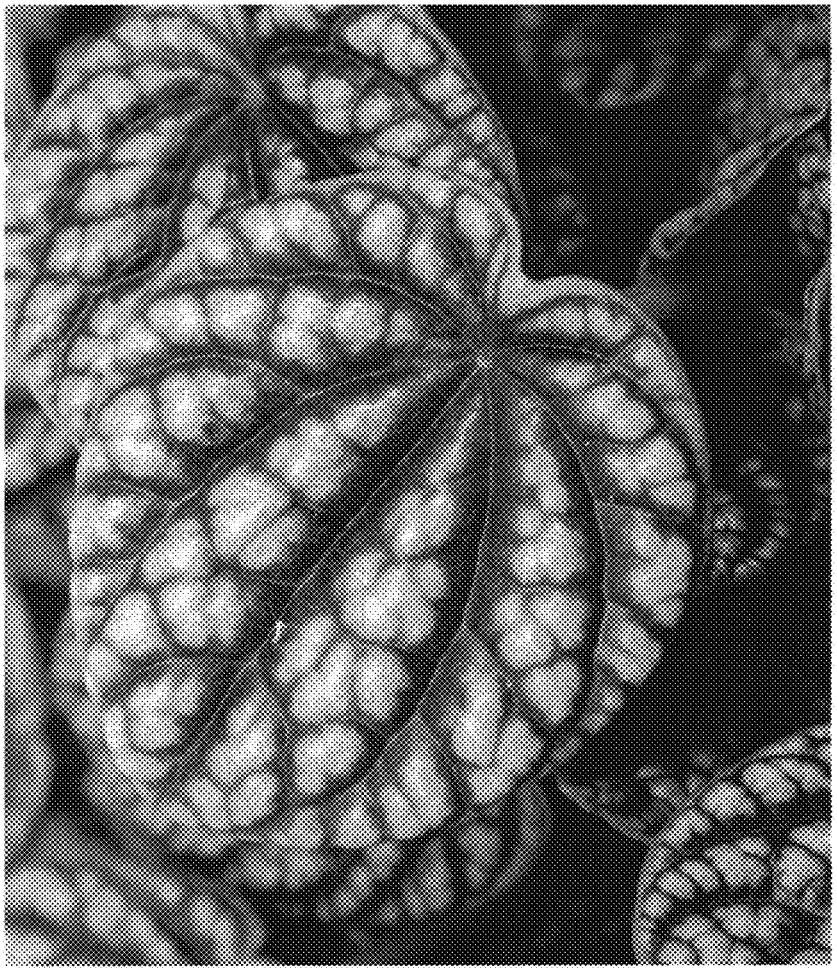

FIG. 2 illustrates a close up of the foliage.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-1904' plants at 52 weeks of age, grown in a greenhouse in Sappemeer, the Netherlands during August of 2019. The growing temperature ranged from 17° C. to 20° C. at night to 19° C. to 21° C. during the day. Measurements and numerical values represent averages of typical flowering types.

Botanical classification: *Peperomia caperata* 'EC-PEPE-1904'.

PROPAGATION

Time to initiate roots: About 21 days at approximately 20° C. in Summer.

Time to produce rooted cutting: About 25 days at 20° C. in Summer.

Description of roots: Herbaceous, fine, moderately dense, freely branching. White in color, not accurately measured with R.H.S. chart.

PLANT

Plant type: Perennial potted plant.

Plant shape: Flattened globular.

Growth habit: Rosettes of leaves forming very short thick stems.

Plant spread: Approximately 32.5 cm.

Height: 16 cm to top of foliar plane.

Growth rate: Moderate to high.

Plant vigor: Moderate.

Age of plant described: Approximately 52 weeks from a rooted cutting.

Branching habit: Leaves arranged in rosettes, rosettes form very short thick main stems, branching into lateral rosettes of leaves.

Pinching: Not required.

Number of primary (main) branches per plant: Average 22.

Number of secondary (lateral) branches per plant: Average 10.

Lateral stems:

*Length*.—Average: 2 cm.

*Diameter*.—Average: 0.8 cm.

Internode length: Average: Less than 0.1 cm.

Appearance and shape: Succulent, thick and rounded.

Luster: Slightly glossy.

Aspect/angle from vertical: Average 20°.

Strength: Moderately strong.

Color:

*Developing*.—RHS Yellow-Green 148C.

*Mature*.—RHS Yellow-Green 148B to 148C.

*At internodes*.—RHS Yellow-Green 148B to 148C.

Pubescence: None.

FOLIAGE

Leaf:

*Arrangement*.—Alternate, single.

*Quantity*.—Average 12.

*Average length*.—5.6 cm.

*Average width*.—5.1 cm.

*Shape of blade*.—Cordate, perfoliate.

*Apex*.—Broad, bluntly acute.

*Base*.—Cordate, lobes connected thus forming perfoliate leaf.

*Margin*.—Entire, moderately revolute.

*Aspect*.—Very slightly convexed.

*Texture of top surface*.—Glabrous, smooth, moderately leathery, strongly bullate.

*Texture of bottom surface*.—Glabrous, smooth, moderately leathery.

*Pubescence*.—None.

*Luster, upper side*.—Glossy.

*Luster, under side*.—Very slightly glossy, velvety.

*Color*.—Young foliage upper side: RHS Greyed-Green 190B and 190C, veined Green NN137B to NN137C. Young foliage under side: RHS Yellow-Green 147D, main veins tinged Greyed-Purple 183D. Mature foliage upper side: RHS Greyed-Green 188B and N189D. Mature foliage under side: RHS Yellow-Green 147D.

*Venation*.—Type: Parallel, strongly furrowed. Venation color upper side: RHS Greyed-Green N189A. Venation color under side: RHS Greyed-Purple 183B.

*Petiole*.—Average. Length: 12.6 cm. Diameter: 4 mm. Texture: Glabrous, smooth. Strength: Low. Luster: Both sides moderately glossy. Color, upper side: RHS Yellow-Green N148B, moderately finely striped Greyed-Red 182A, more densely towards distal end. Color, under side: RHS Yellow-Green N148B, moderately finely striped Greyed-Red 182A, more densely towards distal end.

FLOWER

No flowers observed to date.

OTHER CHARACTERISTICS

Seeds and fruits: None observed to date.

Disease/pest resistance: No increased nor decreased resistance to normal diseases and pests of *Peperomia* has been observed.

Temperature tolerance: Tolerates temperatures up to 40° C., hardy to at least USDA zone 10. High wind tolerance.

What is claimed is:

1. A new and distinct cultivar of *Peperomia* plant named 'EC-PEPE-1904' as herein illustrated and described.

* * * * *